United States Patent [19]

Roessler et al.

[11] Patent Number: 5,743,994
[45] Date of Patent: Apr. 28, 1998

[54] APPARATUS FOR MAKING AN ABSORBENT ARTICLE WITH ASYMMETRIC LEG ELASTICS

[75] Inventors: Thomas Harold Roessler, Menasha; Paul Theodore Van Gompel, Hortonville; Daniel Robert Schlinz, Greenville; Mark Gordon Heath, Butte des Morts, all of Wis.; Geoffrey Walter Frost, Ogden, Utah

[73] Assignee: Kimberly-Clark Worldwide, Inc., Neenah, Wis.

[21] Appl. No.: 554,110

[22] Filed: Nov. 6, 1995

[51] Int. Cl.$^6$ .................................................... A61F 13/15
[52] U.S. Cl. .................... 156/495; 156/494; 156/516; 156/522
[58] Field of Search ............................. 156/494–496, 156/163, 164, 229, 250, 267, 269, 516, 522; 604/385.2

[56] References Cited

U.S. PATENT DOCUMENTS

| | | |
|---|---|---|
| 3,901,236 | 8/1975 | Assarsson et al. . |
| 4,076,663 | 2/1978 | Masuda et al. . |
| 4,081,301 | 3/1978 | Buell . |
| 4,227,952 | 10/1980 | Sabee . |
| 4,286,082 | 8/1981 | Tsubakimoto et al. . |
| 4,430,086 | 2/1984 | Repke .................. 604/385.2 |
| 4,496,360 | 1/1985 | Joffe et al. . |
| 4,498,944 | 2/1985 | Krause et al. . |
| 4,515,595 | 5/1985 | Kievit et al. . |
| 4,555,244 | 11/1985 | Buell . |
| 4,573,382 | 3/1986 | Kloehn et al. .................. 83/53 |
| 4,578,073 | 3/1986 | Dysart et al. . |
| 4,585,448 | 4/1986 | Enloe . |

FOREIGN PATENT DOCUMENTS

| | | |
|---|---|---|
| 0059014A2 | 9/1982 | European Pat. Off. . |
| 0149999A2 | 7/1985 | European Pat. Off. . |
| 0183668A2 | 6/1986 | European Pat. Off. . |
| 0217032A3 | 4/1987 | European Pat. Off. . |
| 0220950A2 | 5/1987 | European Pat. Off. . |
| 0300615A1 | 1/1989 | European Pat. Off. . |
| 0309246A1 | 3/1989 | European Pat. Off. . |
| 0391476A2 | 10/1990 | European Pat. Off. . |
| 0398392A2 | 11/1990 | European Pat. Off. . |
| 0403832A1 | 12/1990 | European Pat. Off. . |
| 0460467A1 | 12/1991 | European Pat. Off. . |
| 0487921A2 | 6/1992 | European Pat. Off. . |
| 0522584A2 | 1/1993 | European Pat. Off. . |
| 0539703A1 | 5/1993 | European Pat. Off. . |
| 0547497A3 | 6/1993 | European Pat. Off. . |
| 0409876B1 | 7/1993 | European Pat. Off. . |
| 2078811 | 1/1982 | United Kingdom . |
| 2142241 | 1/1985 | United Kingdom . |
| 2215986 | 10/1989 | United Kingdom . |
| 2248380 | 4/1992 | United Kingdom . |
| 2251172 | 7/1992 | United Kingdom . |
| 2253131 | 9/1992 | United Kingdom . |
| 2254997 | 10/1992 | United Kingdom . |
| 85/05254 | 12/1985 | WIPO . |
| 92/07531 | 5/1992 | WIPO . |
| 93/03698 | 3/1993 | WIPO . |
| WO93/05742 | 4/1993 | WIPO . |
| WO93/12746 | 7/1993 | WIPO . |
| WO93/14729 | 8/1993 | WIPO . |
| WO93/21877 | 11/1993 | WIPO . |
| WO94/07450 | 4/1994 | WIPO . |
| WO94/07451 | 4/1994 | WIPO . |

*Primary Examiner*—Jeff H. Aftergut
*Attorney, Agent, or Firm*—Paul Yee

[57] ABSTRACT

A method and apparatus for making an elasticized article includes a delivering mechanism for supplying a substrate web having a longitudinal direction and a lateral cross-direction. A first connecting mechanism attaches an inboard elastic member to said substrate web, and a second connecting mechanism attaches an outboard elastic member to the substrate web, with the outboard elastic member located laterally outboard of the inboard elastic member. A dividing mechanism separates away a portion of the substrate web and a portion of the outboard elastic member to thereby provide a set of elastics which are arranged in a staggered overlapping relation.

17 Claims, 5 Drawing Sheets

U.S. PATENT DOCUMENTS

| | | |
|---|---|---|
| 4,586,199 | 5/1986 | Birring . |
| 4,597,760 | 7/1986 | Buell . |
| 4,597,761 | 7/1986 | Buell . |
| 4,601,717 | 7/1986 | Blevins . |
| 4,608,115 | 8/1986 | Schroth et al. . |
| 4,610,681 | 9/1986 | Strohbeen et al. . |
| 4,626,305 | 12/1986 | Suzuki et al. . |
| 4,642,109 | 2/1987 | Bradley ................................. 604/385.2 |
| 4,642,819 | 2/1987 | Ales et al. . |
| 4,657,539 | 4/1987 | Hasse . |
| 4,661,102 | 4/1987 | Shikata et al. ........................ 604/385.2 |
| 4,662,877 | 5/1987 | Williams . |
| 4,663,220 | 5/1987 | Wisneski et al. . |
| 4,666,542 | 5/1987 | De Jonckheere . |
| 4,666,647 | 5/1987 | Enloe et al. . |
| 4,687,477 | 8/1987 | Suzuki et al. . |
| 4,692,163 | 9/1987 | Widlund et al. . |
| 4,699,823 | 10/1987 | Kellenberger et al. . |
| 4,704,116 | 11/1987 | Enloe . |
| 4,711,683 | 12/1987 | Merkatoris . |
| 4,761,258 | 8/1988 | Enloe . |
| 4,762,582 | 8/1988 | de Jonckheere . |
| 4,795,451 | 1/1989 | Buckley ................................ 604/385.2 |
| 4,795,510 | 1/1989 | Wittrock et al. . |
| 4,798,603 | 1/1989 | Meyer et al. . |
| 4,808,176 | 2/1989 | Kielpikowski . |
| 4,834,736 | 5/1989 | Boland et al. . |
| 4,834,737 | 5/1989 | Khan . |
| 4,834,738 | 5/1989 | Kielpikowski et al. . |
| 4,838,969 | 6/1989 | Nomura et al. . |
| 4,842,596 | 6/1989 | Kielpikowski et al. . |
| 4,846,823 | 7/1989 | Enloe . |
| 4,850,990 | 7/1989 | Huntoon et al. . |
| 4,861,652 | 8/1989 | Lippert et al. . |
| 4,880,420 | 11/1989 | Pomparelli . |
| 4,892,536 | 1/1990 | DesMarais et al. . |
| 4,895,568 | 1/1990 | Enloe . |
| 4,917,696 | 4/1990 | De Jonckheere . |
| 4,935,021 | 6/1990 | Huffman et al. . |
| 4,938,754 | 7/1990 | Mesek ................................... 604/385.2 |
| 5,028,224 | 7/1991 | Pieper et al. . |
| 5,037,415 | 8/1991 | Leroy et al. . |
| 5,055,103 | 10/1991 | Nomura et al. . |
| 5,080,658 | 1/1992 | Igaue . |
| 5,092,861 | 3/1992 | Nomura et al. . |
| 5,100,398 | 3/1992 | Leroy et al. . |
| 5,147,487 | 9/1992 | Nomura et al. . |
| 5,188,626 | 2/1993 | Toyoda et al. . |
| 5,188,627 | 2/1993 | Igaue et al. . |
| 5,226,992 | 7/1993 | Morman . |
| 5,232,777 | 8/1993 | Sipinen et al. . |
| 5,235,515 | 8/1993 | Ungpiyakul et al. . |
| 5,246,431 | 9/1993 | Minetola et al. . |
| 5,275,676 | 1/1994 | Rooyakkers et al. . |
| 5,399,219 | 3/1995 | Roessler et al. . |
| 5,540,672 | 7/1996 | Roessler et al. ..................... 604/385.2 |

APPARATUS FOR MAKING AN ABSORBENT ARTICLE WITH ASYMMETRIC LEG ELASTICS

FIELD OF THE INVENTION

The present invention relates to a process for making elasticized absorbent articles. More particularly, the present invention relates to a process for making absorbent articles having elasticized leg openings.

BACKGROUND OF THE INVENTION

Absorbent articles, such as disposable diapers, have included elasticized leg bands to provide elasticized gathers at the leg openings of the article. Each elasticized leg band can include various types of elastic members, such as single elastomeric strip, multiple elastomeric strips, or multiple elastomeric strands or threads arranged in separated, parallel or non-parallel configurations. The elastic members can be assembled into the article with a linear or curvilinear configuration, and the curved leg elastic members can further include a reflexed curvature. In particular articles, the elastic members can be arranged in selected sets or groups having arrangements in which individual elastic members are offset and longitudinally asymmetrical from one another.

Various conventional techniques have been employed to produce articles having the elastic members arranged to provide selected elasticized regions, such as elasticized waist or leg openings. Particular techniques have been configured to provide the substantially straight, linear elastic members, and other techniques have been configured to provide the curved elastic members.

Conventional techniques for making elasticized articles, such as those described above, however, have not been sufficiently satisfactory for making articles which include a system of asymmetrically positioned elastic members. It has been difficult to reliably and consistently produce the desired size and positioning of the asymmetrical elastics. As a result, there has been a continued need for improved systems for making the desired elasticized and gathered portions of selected articles, such as the elasticized leg bands of disposable diapers.

BRIEF DESCRIPTION OF THE INVENTION

The present invention can provide a distinctive method which includes the steps of supplying a substrate web having a longitudinal direction and a lateral cross-direction, and attaching an inboard elastic member to the substrate web. An outboard elastic member is attached to the substrate web at a location which is laterally outboard of the inboard elastic member. A portion of the substrate web and a portion of the outboard elastic member are separated away to thereby provide a set of elastics which are arranged in a staggered relation.

A further aspect of the invention provides an apparatus for making an elasticized article. The apparatus includes delivering means for supplying a substrate web having a longitudinal direction and a lateral cross-direction. A first connecting means attaches an inboard elastic member to said substrate web, and a second connecting means attaches an outboard elastic member to the substrate web, with the outboard elastic member located laterally outboard of the inboard elastic member. A dividing means separates away a portion of the substrate web and a portion of the outboard elastic member to thereby provide a set of elastics which are arranged in a staggered overlapping relation.

In a particular aspect of the invention, the method and apparatus for making an article includes a mechanism for supplying a substrate web having a first side region and a second side region. A first inboard elastic member is attached to the first side region of the substrate web, and a second inboard elastic member is attached to the second side region of the substrate web. A first outboard elastic member is attached to the first side region of the substrate web, and a second outboard elastic member is attached to the second side region of the substrate web. Each of the outboard elastic members is located laterally outboard of its associated inboard elastic member, respectively. A portion of the first side region of the substrate web and a portion of the first outboard elastic member are separated away to thereby provide a first set of elastics which are arranged in a staggered relation. A portion of the second side region and a portion of the second outboard elastic member are separated away to thereby provide a second set of elastic members which are arranged in a staggered relation.

In its various aspects, the process and apparatus of the present invention can more effectively produce elasticized articles on high-speed manufacturing lines, and can readily construct articles which provide a desired conformity to the different, body lines and shapes which are typically present at the front and back regions of a wearer's body. The process and apparatus can be readily adapted for use with existing manufacturing lines, and can be readily reconfigured to provide elastic systems which include elastic members arranged with desired offsets and asymmetries.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The technique of the present invention will be described in the context of its use in producing disposable absorbent articles, such as those which can be placed against or in proximity to the body of the wearer to absorb and contain various exudates discharged from the body. The articles are intended to be discarded after a limited period of use, and are not intended to be laundered or otherwise restored for reuse. It should be understood, however, that the potential uses of the method and apparatus of the present invention are not limited to disposable absorbent articles. While the present description will particularly be made in the context of a diaper article, it should be further understood that the present invention is also applicable to other articles, such as caps, gowns, covers, adult incontinence garments, sanitary napkins, children's training pants and the like.

Figure 1:
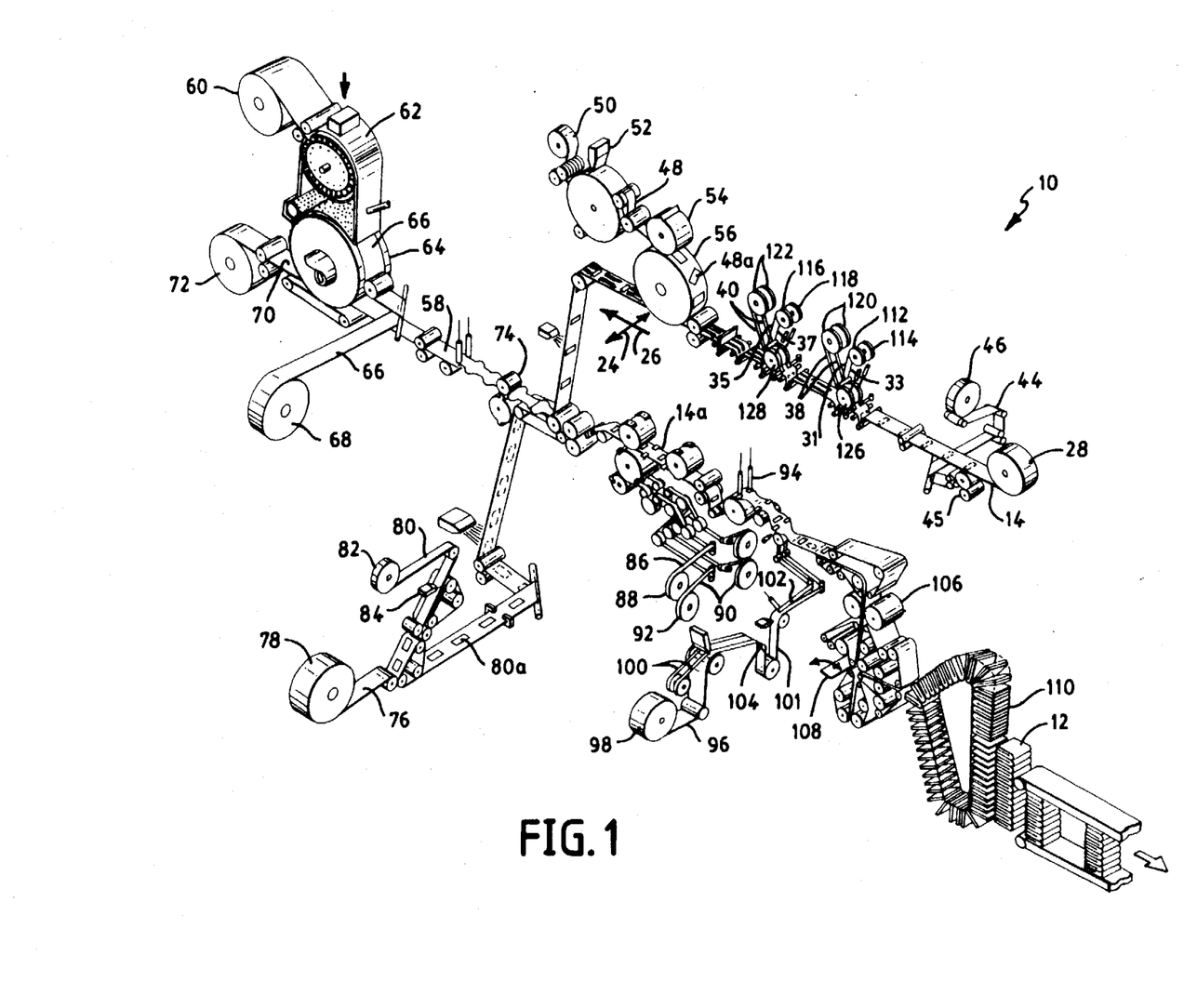
FIG. 1 shows a schematic representation of the method and apparatus of the invention.
Figure 2:
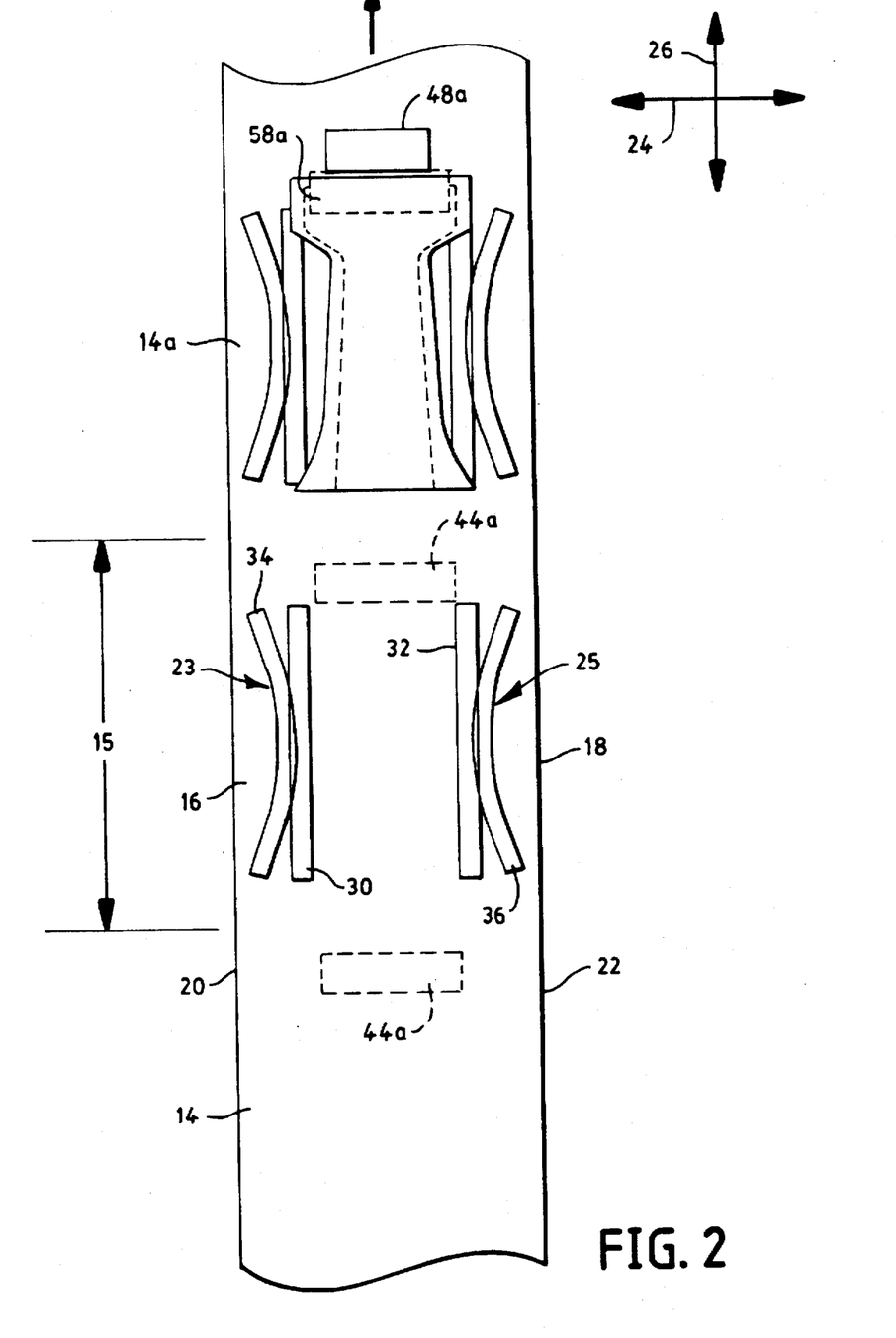
FIG. 2 representatively shows a top, plan view of a substrate web with various components assembled to the web.

With reference to FIGS. 1 and 2, a method and apparatus 10 for making an elasticized article, such as a diaper 12, includes a delivering means for supplying a substrate web 14 having a longitudinal machine-direction 26 and a lateral cross-direction 24. A connecting means, such as a mechanism which includes a first elastic applicator roll 126, attaches and secures an inboard elastic member 30 to the substrate web 14 at a selected location. A second connecting means, such as a mechanism which includes a second elastic applicator roll 128, attaches and secures an outboard elastic member 34 to the substrate web 14 with the outboard elastic member 34 positioned laterally outboard of the inboard elastic member 30. A dividing means, such as a water cutter system 94, separates away a portion of the substrate web 14 and a corresponding, associated portion of the outboard elastic member 34 to thereby provide a set of elastics which are arranged in a staggered, overlapping relation.

The method and apparatus of the invention can be configured to produce a plurality of sets of elastics with each set including an inboard elastic member and an associated outboard elastic member arranged in a staggered overlapping relation. For example, an article such as the shown diaper 12, can include two sets of elastics with one set located at each of a pair of laterally opposed side margin regions of the diaper. The second set of elastics in the second side margin of the article has a configuration which is substantially a mirror image of the first set of elastics located in the first side margin of the diaper.

Accordingly, a particular aspect of the invention provides a method and apparatus 10 for making an elasticized article, such as the shown diaper 12. The method and apparatus include a delivery mechanism, such as a mechanism which includes supply roll 28, for supplying a substrate web 14 having a first side region 16 and a second side region 18. A first connecting means, such as a mechanism which includes the applicator roll 126, attaches a first inboard elastic member 30 to the first side region 16 of the substrate web 14, and attaches a second inboard elastic member 32 to the second side region 18 of the substrate web. A second connecting means, such as the mechanism which includes applicator roll 128, attaches a first outboard elastic member 34 to the first side region 16 of the substrate web 14, and attaches a second outboard elastic member 36 to the second side region 18 of the substrate web. Each of the outboard elastic members 34 and 36 is located laterally outboard of its associated inboard elastic member 30 and 32, respectively. A dividing means, such as the shown water cutter system 94, separates away a portion of the first side region 16 of the substrate web 14, and a portion of the first outboard elastic member 34 to thereby provide a first set 23 of elastics which are arranged in a staggered, overlapping relation. The dividing means also separates away a portion of the second side region 18 and a portion of the second outboard elastic member 36 to thereby provide a second set 25 of elastic members which are arranged in another staggered, overlapping relation.

In the construction and assembly of the various webs and component elements employed to form article 12, various attaching or securing mechanisms can be employed. Such attaching mechanisms can, for example, include adhesive bonding, cohesive bonding, thermal bonding, sonic bonding, stitching, pinning, stapling, welding bonds, fusing bonds, and the like. An example, of a typical construction adhesive is a conventional hotmelt, pressure-sensitive adhesive.

At any particular, selected location along the method and apparatus, the machine-direction 26 is the generally lengthwise direction along which a particular web, or composite web, of material is being moved or transported through the process. The cross-direction 24 extends generally along the plane of the web of material, and is perpendicular to the particular machine-direction established by the method or apparatus at the selected location.

The inboard elastic members 30, 32 and the outboard elastic members 34, 36 are typically arranged to operably gather and shirr the substrate web 14. In the illustrated arrangement, the elastic members are arranged to gather the substrate web along its longitudinal, machine-direction 26. Optionally, the present invention can be configured to provide other elastic members which are arranged to gather the substrate web along its lateral, cross-direction 24.

With reference to the configuration of the invention representatively shown in FIGS. 1 and 2, a substrate web 14 is suitably delivered from a suitable source, such as the shown supply roll 28 and is moved at a predetermined speed along the longitudinal, machine-direction 26 of the method and apparatus. The substrate web can, for example, be a web of the material employed to form a selected portion of the final article, such as the topsheet, backsheet or other layer of a diaper article. In the shown arrangement of the invention, the substrate web 14 is selected to provide the backsheet or outer cover of the article. Accordingly, the substrate web may be composed of a liquid permeable material, but desirably comprises a material which is configured to be substantially impermeable to liquids. For example, a typical backsheet can be manufactured from a thin plastic film, or other flexible liquid-impermeable material. Such "flexible" materials are compliant and will readily conform to the general shape and contours of the wearer's body.

In particular embodiments of the invention, substrate web 14 can be a polyethylene film having a thickness of from about 0.012 millimeters (0.5 mil) to about 0.051 millimeters (2.0 mils). In the shown embodiment, for example, the substrate web is a film having a thickness of about 1.25 mil. Alternative constructions of the substrate web may comprise a woven or non-woven fibrous web layer which has been totally or partially constructed or treated to impart a desired level of liquid impermeability to selected regions of the substrate web that are adjacent or proximate the absorbent body. The substrate web 14 typically provides the outer cover of the article. Optionally, however, the article may comprise a separate outer cover member which is in addition to the substrate web.

The substrate web 14 may optionally include a microporous, "breathable" material which permits vapors to escape from the absorbent structure while still preventing liquid exudates from passing through the substrate web. For example, the breathable substrate web may be composed of a microporous polymer film or a nonwoven fabric which has been coated or otherwise treated to impart a desired level of liquid impermeability. An example of a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The substrate web can also be embossed or otherwise be provided with a matte finish to exhibit a more aesthetically pleasing appearance.

The substrate web 14 includes a plurality of appointed article length segments 15 (FIG. 2) which are serially connected and distributed along the longitudinal machine-direction 26 of the substrate web. Each of the article segments 15 is typically appointed to be separated away to form an individual article, such a diaper 12.

With reference to FIGS. 1 and 2, the present invention can be configured to provide a patch 44a of landing zone material onto a selected inward-side or outward-side surface of the substrate web 14. In the shown arrangement, the landing zone patch is positioned on the outward-side surface of the substrate web, and is composed of a material which is compatible with the fastening system employed with the final article 12. The fastening system may, for example, comprise an adhesive, cohesive, an interengaging mechanical fastening mechanism or the like. As appropriate, the landing zone material is operably compatible with the selected adhesive or cohesive, or is composed of a cooperating component of the mechanical fastener. For example, the landing zone material may be the hook or loop component of a hook-and-loop fastening system.

In the representatively shown arrangement, a web of the landing zone material 44 is delivered from a suitable source, such as the shown supply roll 46, and is transported to an operable cutting mechanism 45. The cutting mechanism separates the landing zone web 44 into a plurality of discreet patches 44a (FIG. 2) which are then operably attached to predetermined, sequential locations along the substrate web 14. Suitable techniques for cutting and placing the landing zone patches 44a on to the substrate web 14 are described in U.S. Pat. No. 4,795,510 entitled PROCESS FOR APPLYING REINFORCING MATERIAL TO A DIAPER COVER MATERIAL, and issued Jan. 3, 1989 to M. Wittrock et al.; and in U.S. Pat. No. 5,235,515 entitled METHOD AND APPARATUS FOR CONTROLLING THE CUTTING AND PLACEMENT OF COMPONENTS ON A MOVING SUBSTRATE, AND ARTICLE MADE THEREWITH, and issued Aug. 10, 1993 to T. Ungpiyakul et al. (Attorney docket No. 10,159). The entire disclosures of these documents are hereby incorporated by reference in a manner which is consistent herewith.

The substrate web 14 is transported to a suitable mechanism for operably locating and attaching elastic members to intermittent, spaced apart locations along the machine-direction of the web. In the shown configurations, the spacing technique includes a mechanism for intermittently forming a selected plurality of laterally extending tucks 42 (FIGS. 4 and 5) in the substrate web, and then removing the tucks after the elastics have been applied to the substrate web. Suitable techniques for assembling stretched elastic members to the laterally opposed side regions of a moving substrate web described in U.S. Pat. No. 4,227,952 entitled METHOD AND APPARATUS FOR MAKING DIAPERS WITH ELASTIC BANDS issued Oct. 14, 1980 to R. Sabee; and U.S. Pat. No. 4,498,944 entitled METHOD AND APPARATUS FOR PRODUCING AN ELASTICIZED GARMENT BY TUCKING A PORTION OF THE DIAPER WEB DURING BONDING OF ELASTIC TO THE UN-TUCKED PORTIONS OF THE WEB issued Feb. 12, 1985 to C. Krause et al., the entire disclosures of which are hereby incorporated by reference in a manner which is consistent herewith. Other suitable manufacturing techniques for assembling stretched elastic members to a moving substrate web are described in U.S. Pat. No. 4,081,301 entitled METHOD AND APPARATUS FOR CONTINUOUSLY ATTACHING DISCREET, STRETCHED ELASTIC STRANDS TO PREDETERMINED ISOLATED PORTIONS OF DISPOSABLE ABSORBENT PRODUCTS issued Mar. 28, 1978 to K. Buell; and U.S. Pat. No. 4,711,683 entitled METHOD AND APPARATUS FOR MAKING ELASTIC DIAPERS issued Dec. 8, 1987 to J. Merkatoris.

The various elastic members are secured to the substrate web 14 in an elastically contractible condition so that in a normal under strain configuration, the elastic members effectively contract against the substrate web. The elastic members can be secured in the elastically contractible condition in various ways. For example, the elastic members may be stretched and the stretched elastics secured to the substrate web 14 while the substrate web is in an uncontracted condition. Alternatively, the substrate web may be contracted, for example, by pleating, and the elastic members secured and connected to the substrate web while the elastic members are in their unrelaxed or unstretched condition. Still other mechanisms, such as heat-shrink elastic material, may be attached to an uncontracted substrate web and then activated to gather the appointed regions of the substrate web.

In the configuration illustrated in FIG. 1, the elastic members are arranged to extend essentially along the complete length of an appointed crotch region of a diaper article. Alternatively, the elastic members may extend the entire length of the article, or any other length suitable for providing the arrangement of elastically contractible lines desired for the particular article design.

The various elastic members may have any of a multitude of configurations. For example, the width of the individual elastic members may be varied from 0.25 millimeters (0.01 inches) to 25 millimeters (1.0 inches) or more. Each elastic member may comprise a single strand or strip of elastic material, or may comprise a plurality of parallel or non-parallel strands of elastic material. The elastic members may be applied in a rectilinear or curvilinear arrangement. Where multiple strands are employed, the individual strands may be constructed to provide substantially equal elastic forces, or may be constructed to provide different elastic forces. For example, the individual strands may be of different diameter or other size, or may be configured with different amounts of elongation to thereby provide a gradient or other variation of elastic tensions. Where the strands are non-parallel, two or more of the strands may intersect or otherwise interconnect within the elastic member. The elastic members may be affixed to the substrate web 14 in any of several conventional ways which are known in the art. For example, the elastic members may be ultrasonically bonded, heat and pressure sealed using a variety of bonding patterns, or adhesively bonded to the substrate web with sprayed or swirled patterns of hotmelt or other type of adhesive.

In the illustrated configuration of the invention, for example, the elastic members may comprise a carrier sheet to which are attached a grouped set of elastics composed of a plurality of individual elastic strands. The elastic strands may intersect or be interconnected, or be entirely separated from one another. The carrier sheet may, for example, comprise a 0.002 cm thick film of unembossed polypropylene material. The elastic strands can, for example, be composed of LYCRA® elastomer available from DuPont, a business having offices in Wilmington, Del. Each elastic strand is typically within the range of about 620–1050 decitex (dtx), and preferably, is about 940 dtx in an embodiment of the invention wherein three strands are employed for each elasticized legband. In addition, the elastic members may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may be offset by a selected distance toward either the front or rear waistband of the diaper to provide desired fit and appearance.

The configuration of the invention representatively shown in FIG. 1 provides a system of leg elastic members which are each composed of multiple strands of elastomeric material attached to a thin, flexible carrier sheet. To form the inboard elastic members 30 and 32 (FIG. 2), a first inboard elastic web 31 is operably delivered from a suitable source, such as the shown supply roll 112, and a second inboard elastic web 33 is operably delivered from a suitable source, such as the shown supply roll 114. Each of the elastic webs 31 and 33 is composed of multiple strands of elastomeric material, such a Lycra®, and the individual strands are arranged in a substantially parallel, spaced-apart and separate relation to each other.

A pair of inboard carrier sheet ribbons 38 are operably delivered from suitable sources, such as the shown supply rolls 120. The carrier ribbons are operably attached to the inboard elastic webs 31 and 33, and the resultant composites are attached to the substrate web 14. In the shown arrangement, the inboard composite webs are substantially straight and are located at the laterally opposed side regions 16 and 18 of the substrate web 14. With respect of each article segment 15 of the substrate web, appointed portions of the assembled composite webs provide a pair of laterally opposed inboard elastic members 30 and 32 having a substantially straight and linear configuration.

To form the outboard elastic members 34 and 36 (FIG. 2), a first outboard elastic web 35 is operably delivered from a suitable source, such as the shown supply roll 116, and a second outboard elastic web 37 is operably delivered from a suitable source, such as the shown supply roll 118. Each of the elastic webs 35 and 37 can be composed of multiple strands of elastomeric material, such a Lycra®, and the individual strands can be arranged in a substantially parallel, spaced-apart and separate relation to each other.

Outboard carrier sheet ribbons 40 are operably delivered from a suitable source, such as the shown supply rolls 122, and are operably mated and attached to the corresponding outboard elastic webs 35 and 37. The resultant outboard composite webs are operably delivered for attachment onto the laterally opposed side regions 16 and 18 of the substrate web 14. In the representatively shown configuration of the invention, each outboard elastic web 35 and 37 is in a laterally offset and spaced-away position which is laterally outboard of its corresponding and associated inboard elastic web 31 and 33, respectively.

In the shown arrangement, the outboard elastic webs at each appointed article segment 15 of the substrate web 14 are selectively curved to include sections thereof which laterally diverge from its associated inboard elastic web. A suitable technique for forming a stretched, curved elastic to a substrate is described in U.S. Pat. No. 5,275,676 entitled METHOD AND APPARATUS FOR APPLYING A CURVED ELASTIC TO A MOVING WEB issued Jan. 4, 1994 to J. Rooyakkers et al. The entire disclosure of which is hereby incorporated by reference in a manner which is consistent herewith.

While not being required for the technique of the present invention, various other components may also be assembled onto the substrate web 14. For example, waist elastic members, absorbent pads, a liquid permeable topsheet layer, sections of surge management material, and fastening mechanisms for securing the article on a wearer may be incorporated onto the substrate web 14 by employing various conventional techniques arranged in an operable sequence, as desired.

For example, the shown configuration of the invention includes a mechanism for locating and attaching patches of elastic material onto the substrate web 14 to form the waist elastic members at the front and rear waist band sections of the diaper. Suitable materials for forming the waist elastic members are described in U.S. Pat. No. 4,861,652 entitled DIAPER ARTICLE WITH ELASTICIZED WAIST PANEL, and issued Aug. 29, 1989 to M. Lippert et al., the entire disclosure of which is incorporated herein by reference in a manner which is consistent herewith.

In the arrangement shown in FIG. 1, the waist elastic web 48 is operably delivered from a suitable source, such as the shown supply roll 50, and is moved to a adhesive applicator system 52 which places an assembly adhesive onto the waist elastic web 48. The waist elastic web is delivered to a cutting mechanism 54 which separates the waist elastic web 48 into discrete patches 48a for attachment to the substrate web 14. The web 48 of elastic material is elastically contractible along its longitudinal machine-direction. Accordingly, the patches 48a of waist elastic material are delivered onto a rotating turn roll 56 to reorient the elastic contractibility of the waist elastic material along the cross-direction 24 of the substrate web 14. A suitable rotating turn roll is described in U.S. Pat. No. 4,608,115 entitled REVOLVING TRANSFER ROLL, and issued Aug. 26, 1986 to Schroth et al., the entire disclosure of which is incorporated herein by reference in a manner which is consistent herewith.

A series of absorbent pads can also be assembled onto the substrate web 14. In the illustrated embodiment, a sheet of wood pulp material 60 is delivered into a conventional fiberizing mechanism, such as hammermill 62. The hammermill disintegrates the wood pulp sheet into a multiplicity of individual fibers which are air laid onto a web of forming tissue 66 carried on the surface of a forming drum 64. The forming tissue 66 is delivered from a suitable source, such as the shown supply roll 68, and is operably placed onto the moving outer surface of the rotating forming drum 64 employing conventional mechanisms. The forming drum 64 delivers the airlaid fibrous web and forming tissue for placement onto a moving web of cover tissue 70 which is operably delivered from a suitable source, such as the shown supply roll 72.

Examples of suitable techniques for forming the airlaid fibrous web are described in U.S. Pat. No. 4,666,647 entitled APPARATUS AND METHOD FOR FORMING A LAID FIBROUS WEB, and issued May 19, 1987 to K. Enloe et al.; and in U.S. Pat. No. 4,761,258 entitled CONTROLLED FORMATION OF LIGHT AND HEAVY FLUFF ZONES, and issued Aug. 2, 1988 to K. Enloe. The entire disclosures of these documents are incorporated herein by reference in a manner which is consistent herewith.

The composite absorbent pad web 58 is delivered to a suitable shaping mechanism, such as a water cutter 74, to produce the desired side contours of the individual absorbent pads. The absorbent pad web 58 is operably divided into individual absorbent pads 58a and assembled onto a moving topsheet web 76.

The topsheet web is typically composed of a fibrous liquid permeable material and is delivered from a suitable source, such as the shown supply roll 78. The topsheet web 76 presents a body-facing surface which is compliant, soft-feeling, and non-irritating to the wearer's skin. Further, the topsheet web can be less hydrophilic than the absorbent pad material, and is sufficiently porous to be liquid permeable, permitting liquid to penetrate through its thickness. A suitable topsheet may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet web material is typically employed to help isolate the wearer's skin from liquids held in the absorbent pads. Various woven and nonwoven fabrics can be used for the topsheet web 76. For example, the topsheet web may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet web fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, the topsheet web 76 can be a nonwoven, spunbond polypropylene fabric composed of about 2.8–3.2 denier fibers formed into a web having a basis weight of about 22 gsm and density of about 0.06 gm/cc. The fabric can be surface treated with a selected amount of surfactant, such as about 0.28% Triton X-102 surfactant. The surfactant can be applied by any conventional means, such as spraying, printing, brush coating or the like. surfactant material, such as a conventional wetting agent, can be applied to a medial section of the topsheet layer 76 to provide a greater wettability of the medial section, as compared to a remainder of the topsheet layer 76. In particular configurations, the cross-directional width of the medial section can be substantially equal to or less than the cross-directional width of a surge management portion 80a, which is constructed from a web of surge management material 80. The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

In desired arrangements, the web of surge management material 80 is delivered from a suitable source, such as the shown supply roll 82, and individual surge management portions 80a are cut from the web 80 and assembled onto the topsheet web 76. In the shown arrangement, for example, an applicator 84 provides an adhesive for securing the surge management portions 80a onto the topsheet web. The resultant, composite topsheet web is delivered for attachment in an arrangement which sandwiches the series of absorbent pads between the topsheet web 76 and the substrate web 14 to provide an assembled substrate web 14a. In the shown configuration, the surge management material is interposed between the topsheet web 76 and the absorbent pads. Optionally, the topsheet web can be interposed between the surge management material and the absorbent pads.

Various woven and nonwoven fabrics can be used to construct the surge management web 80. For example, the surge management web material may be a layer composed of a meltblown or spunbonded web of polyolefin fibers. The surge management layer may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch (about 2.54–7.62 cm). The surge management web may be composed of a substantially hydrophobic material, and the hydrophobic material may optionally be treated with a surfactant or otherwise processed to impart a desired level of wettability and hydrophilicity. In particular configurations of the invention, the surge material can include bicomponent fibers. For example, polypropylene/polyethylene bicomponent fibers may be employed to form the bicomponent fiber portion of any of the described fabrics. In addition, the bicomponent fibers may be flat crimped or helically crimped.

The shown configuration of the surge management material is operably connected to the topsheet web with a conventional pattern of adhesive, such as a swirl adhesive pattern. In addition, the surge management material can be operably connected with a conventional pattern of adhesive to the bodyside surface of the cover tissue 70 employed to construct the absorbent pads. Typically The amount of adhesive add-on should be sufficient to provide the desired levels of bonding, but should be low enough to avoid excessively restricting the movement of liquid from the topsheet layer, through the surge management portion and through the wrapsheet layer.

In the various configurations of the invention, the surge management material may extend over the complete length of the absorbent pad, or may extend over only a part of the absorbent pad length. Where the surge management material extends only partially along the length of the absorbent pad, the surge management material may be selectively positioned anywhere along absorbent pad structure. For example, the surge management material may function more efficiently when it is offset toward the front waistband of the garment and transversely centered within a front section of the absorbent structure. Thus, the surge management material can be approximately centered about the longitudinal center line of absorbent structure, and positioned primarily in a central region of a front section of the absorbent structure.

In other aspects of the invention, the end edges of the surge management material can be spaced longitudinally inboard from the end edges of the individual absorbent pads. In particular configurations, the corresponding, relatively adjacent front end edge of surge management portion 46 can be spaced a predetermined discrete distance from a front waistband end edge of its associated absorbent pad.

Additional details regarding the surge materials and suitable techniques for determining the above-described parameters are set forth in U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of which are hereby incorporated by reference in a manner that is consistent herewith.

With reference to FIG. 2, each article segment 15 of the assembled substrate web 14a is operably constructed to include appointed portions of the inboard elastic webs 31 and 33, and each article segment also includes appointed portions of the outboard elastic webs 35 and 37. With respect to each article segment, a portion of elastic web 31 is arranged to provide the first inboard elastic member 30, a portion of elastic web 33 is arranged to provide the second inboard elastic member 32, a portion of elastic web 35 is arranged to provide the first outboard elastic member 34, and a portion of the elastic web 37 is arranged to provide the second outboard elastic member 36.

The appointed portions of one or more of the elastic webs can extend along substantially the entire length of their associated article segments 15, or any selected portion thereof, as desired. In the illustrated configurations, for example, the elastic web portions are each configured to extend along an intermediate, longitudinally medial portion of each article segment 15.

In the various alternative configurations of the invention, the inboard elastic members 30 and 32, the outboard elastic members 34 and 36, or combinations thereof can be constructed to have a curved configuration. The shown arrangement, for example, is configured to provide inboard elastic members 30 and 32 which have a substantially straight, linear configuration, and to provide outboard elastic members 34 and 36 which have the curved configuration. The representatively shown, curved outboard elastic members are inwardly bowed with respect to the lateral cross-direction 24, and are concave with respect to the laterally outward direction at their longitudinally medial regions. The shown outboard elastic members also have a substantially, continuously curved configuration.

With respect to each article segment 15 of the substrate web 14, the first set 23 of elastic members are arranged to shirr and gather the first side region 16 of the substrate web, and the second set 25 of elastic members are arranged to shirr and gather the second side region 18 of the substrate web.

Suitable fastening mechanisms, such as fastening tapes can then be secured to appointed regions of the assembled substrate web 14a in a conventional manner.

Alternatively, the fastening system may incorporate a stretchable side panel secured to the lateral side regions of each article segment 15 of the substrate web 14. An example of a suitable technique for producing the fastening system is described in U.S. patent application Ser. No. 415,383 filed Apr. 3, 1995 by D. Fries and entitled AN ASSEMBLY PROCESS FOR A LAMINATED TAPE, the entire disclosure of which is incorporated herein by reference in a manner which is consistent herewith.

In the arrangement shown in FIG. 1, a pair of fastener, adhesive tape webs 86 are delivered from supply rolls 88, and a pair of release tape webs 90 are delivered from supply rolls 92. For each side of the diaper, a fastener tape web and a release tape web are assembled together and separated into individual fastener tape assemblies which are attached to appointed, spaced-apart side regions of the assembled substrate web at each article segment 15 in a conventional manner. Accordingly, a pair of fastener tapes are available at each lateral side edge of the diaper 12 at a selected waist band portion of the diaper.

Figure 3:
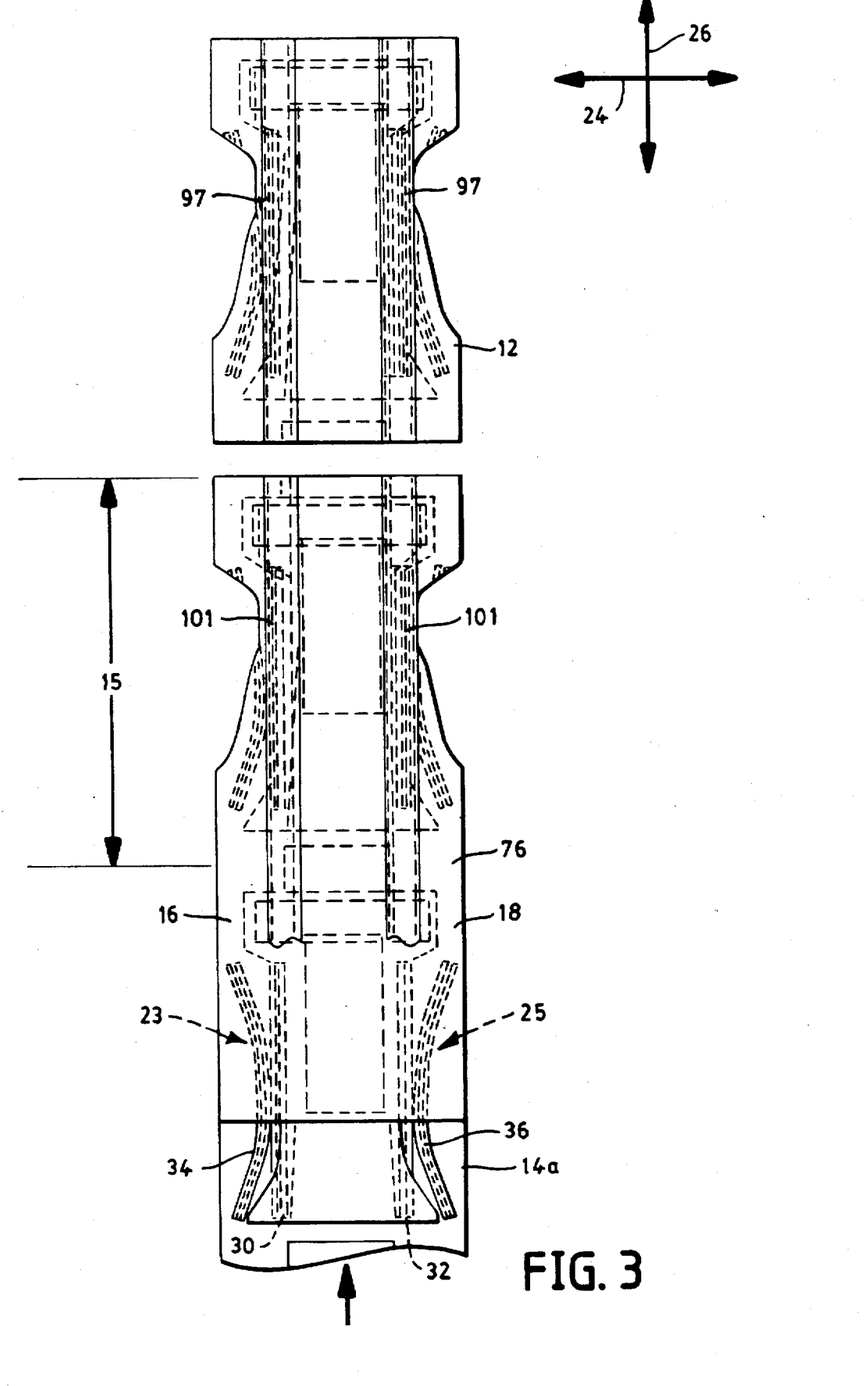
FIG. 3 representatively shows a top, plan view of a composite substrate web having additional components assembled to the web.

The assembled substrate web 14a is delivered to a suitable shaping mechanism, such as water cutter 94 which provides a desired contoured shape to each of the terminal side edges of the assembled substrate web. Accordingly, the web cutter 94 provides a desired, contour to the terminal side edges 20 and 22 of the remaining substrate web 14, and the contour can be configured to have an irregular or regular pattern, as desired. In the shown configuration, the contour has a substantially regularly repeating pattern which provides a selected contour shape that is regularly repeated for each article segment 15 of the assembled substrate web. The shown contours along the first and second side regions of the substrate web are substantially mirror-images of each other. In addition, the contour shape can be asymmetrical with respect to the longitudinal dimension 26 of the article segment 15. Particular aspects of the invention can be configured to have the deepest, most inboard portion of the cut contour located toward the end of the article segment that is appointed to be the front waistband portion of the article 12 (FIG. 3).

Web cutter 94 and its conventional associated mechanisms operably remove selected portions of the assembled substrate web 14a at each article segment 15 of the substrate web 14. In particular, the web cutters 94 are configured to separate away a portion of the first side region 16 of the substrate web 14 and a selected end portion of the first outboard elastic member 34 to thereby provide a first set 23 of elastic members which are arranged in a desired, staggered overlapping relation. In the representatively shown arrangement, the cut pattern is configured to cut away a substantial portion of a selected, longitudinal end portion of the outboard elastic member. As a result, the major section of the remaining outboard elastic is longitudinally biased toward one end of its associated article segment 15. The remaining outboard elastic is desirably biased toward the end of the article segment which is appointed to be at the rear waistband section of the finished article 12. During the separating operation, the web cutter 94 may also separate away portions of other components, such as a portion of the topsheet web 76 at each article segment 15 of the substrate web.

Similarly, another portion of the water cutter system 94 can separate away a portion of the second side region 18 of the assembled substrate web at each article segment 15 of the substrate web 14. In particular, the water cutter 94 can separate away a portion of the second side region 18 of the substrate web 14 and a selected end portion of the second outboard elastic member 36 to thereby provide a second set 25 of elastic members which are arranged in a desired, staggered overlapping relation.

Other cutting mechanisms, such as slitters, die cutters, air knives, lasers, other focused energy beams, and the like may be employed to separate away the selected portions of the substrate 14 and the selected portions of the outboard elastic members 34 and 36.

With respect to each set 23 and 25 of elastics (FIGS. 2 and 3), the first set 23 is arranged to gather and shirr the first side region 16 of the substrate web 14, and the second set 25 is arranged to gather and shirr the second side region 18 of the substrate web. In addition, each outboard elastic member 34, 36 has at least a portion thereof which is in a laterally offset, spaced-away position relative to its associated inboard elastic member 30, 32, respectively. The shown arrangement has the longitudinal end portion of the outboard elastic laterally spaced from its associated inboard elastic. Alternatively, a substantial entirety of the outboard elastic may be laterally spaced from its associated inboard elastic.

In addition, the longitudinally staggered relation between each outboard elastic member and its associated inboard elastic member can be configured with each outboard elastic member overlapping only a portion of its associated, corresponding inboard elastic member. In the shown configuration, the staggered relation is configured with the inboard elastic member 30, 32 overlapping a substantial entirety of the outboard elastic member 34, 36. Alternatively, the staggered relation can be configured with the inboard elastic member 30, 32 biased toward one end of its associated article segment to thereby overlap only a portion of the outboard elastic member 34, 36.

As representatively shown in FIGS. 1 and 3, a pair of containment flaps 97 may be connected to the topsheet web 76. In the illustrated configuration, a containment flap web 96 is delivered from supply roll 98, and two sets of containment flap elastics 100 are assembled and attached onto the containment flap web 96. Each of the two lateral side regions of the containment flap web 96 are folded over inwardly on top of the containment flap elastics 100 and operably secured in place. The folded containment flap web is then slit longitudinally along its medial section between the two sets of containment flap elastics 100 with a suitable separating mechanism, such as slitter 102. The cutting operation provides a pair of containment flap assemblies 101 which are then assembled and attached to the topsheet web 76.

Suitable configurations of the containment flaps 97 are described in U.S. Pat. No. 4,704,116 entitled DIAPERS WITH ELASTICIZED SIDE POCKETS issued Nov. 3, 1987 to K. Enloe; and U.S. patent application Ser. No. 208,816 of K. Everett et al. filed Mar. 4, 1994 and entitled ABSORBENT ARTICLE HAVING AN IMPROVED SURGE MANAGEMENT (Attorney docket No. 11,375). The entire disclosures of these documents are hereby incorporated by reference in a manner that is consistent herewith.

The assembled substrate web can then be delivered to a conventional folding mechanism which folds the assembled substrate web inwardly along a longitudinal fold line. The folded web can then be delivered to a cutting mechanism 106 which separates the assembled substrate web into a series of separate, individual articles 12. The individual articles can then be delivered to a conventional folder mechanism 108 which folds the individual articles along selected lateral fold lines. The folded diapers can subsequently be delivered to a conventional stacker mechanism 110 which aggregates the individual articles into stacks containing a selected number of articles. The stacked articles can then be delivered for packaging in a conventional manner.

Figure 4:
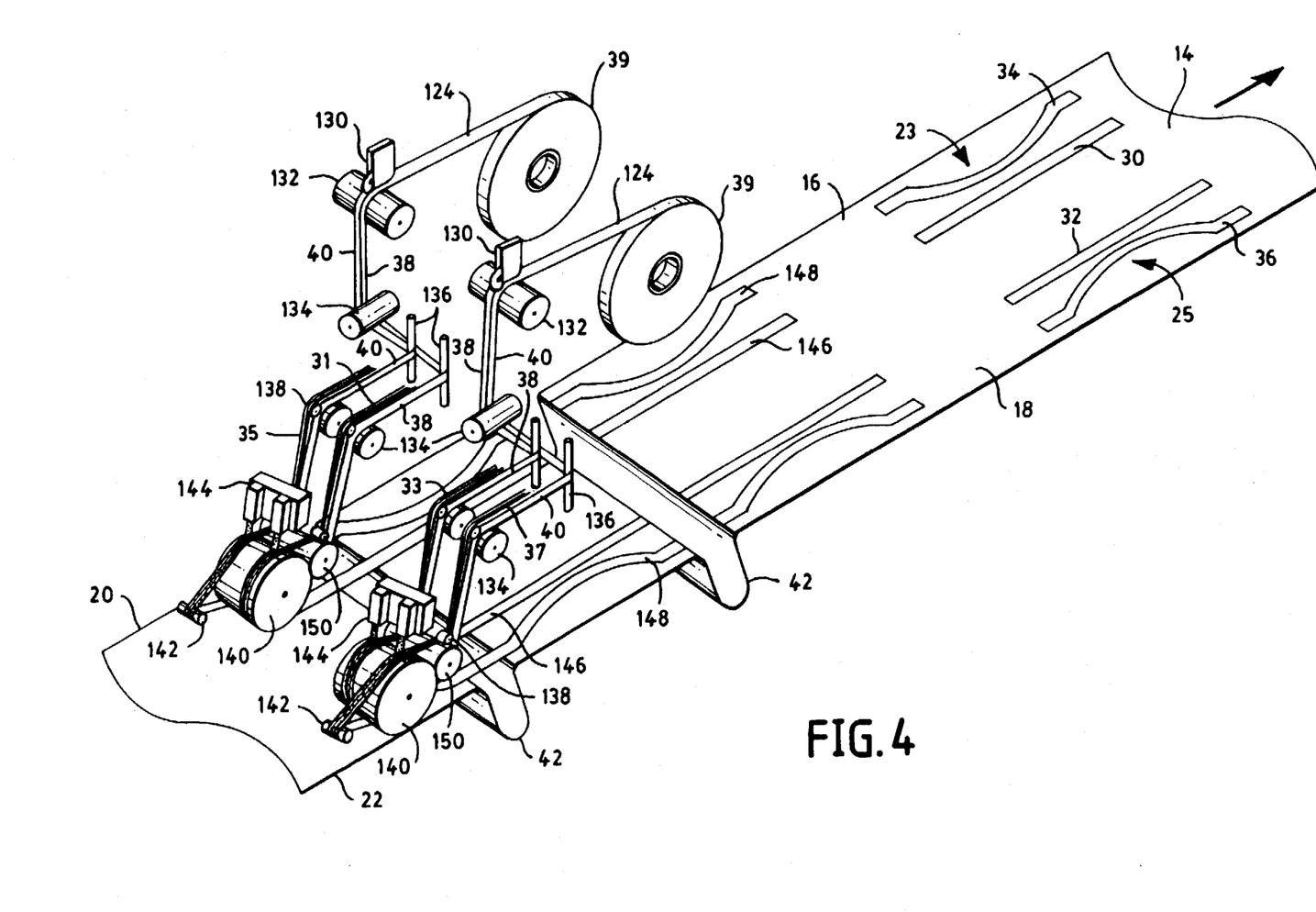
FIG. 4 representatively shows an alternative technique for providing inboard and outboard elastic members onto the substrate web.

With reference to FIG. 4, an alternative technique can be employed to produce a set of inboard and outboard elastic members. In particular, the alternative configuration can be substituted for the elastic applicating system which includes applicator rolls 126 and 128, and their associated components. The system of components representatively shown in FIG. 4 is configured for providing a set of inboard and outboard elastic members along one side region 18 of the substrate web 14 with a single applicator roll 140. It should be readily appreciated that a similar mirror-image arrangement of components can also be employed to provide a second, complementary set of inboard and outboard elastic members along the opposite side region 16 of the substrate web.

The mirror-image system may employ a variation of the applicator roll 140 which is extended to operably reach to the second side region 16 of the substrate web, or may employ another separate applicator roll which may or may not be independently driven.

The representatively shown technique includes a mechanism for delivering a carrier sheet web 124 from a suitable source, such as the shown supply roll 39. A separating means, such as provided by the illustrated rotary slitter 130 and anvil roll 132, operably divides the carrier sheet web into an inboard carrier sheet 38 and an outboard carrier sheet 40. A suitable system of guide rollers 134 direct the inboard and outboard carrier sheets to a separating means, such as provided by the shown separator bars 136. The separating means positions the carrier sheets with a selected cross-directional spacing therebetween, and the particular spacing is appropriately configured to provide the desired spacing between the inboard and outboard elastic members in the final, assembled article 12. The inboard elastic web 33 and the outboard elastic web 37 are delivered from suitable supply rolls, and in the shown arrangement, each of the elastic webs is composed of a predetermined plurality of individual elastic strands.

The carrier sheets 38 and 40 are directed by guide roller 150 onto the outer peripheral surface a rotatable applicator roll 140, which is operably driven with a conventional mechanism, such as an electric motor or the like, to substantially match the peripheral surface speed of the applicator roll to the movement speed of the substrate web 14. A suitable system of guide rollers 138 direct the elastic webs 33 and 37 onto their appointed carrier sheets 38 and 40, respectively, and an attachment means, such as provided by a system of adhesive applicators 144, secures the elastic webs onto the associated carrier sheets. In the shown arrangement, for example, the attachment can be provided by a sprayed or swirled pattern of hotmelt adhesive, and the adhesive can also serve to attach the resultant inboard elastic composite 146 and the outboard elastic composite 148 onto the substrate web 14.

In the shown configuration, the inboard elastic composite 146 is carried on the outer surface of the applicator roll 140 for placement and pressing onto the substrate web along a substantially straight line. The outboard elastic composite 148 is directed to an oscillator roll 142 which moves laterally in a periodic pattern and carries the outboard elastic composite to impart a corresponding, oscillating movement to the outboard elastic composite. For example, the roll 142 may be carried on a swinging arm to produce the desired periodic back-and-forth movement. The oscillating composite is directed back to the surface of the applicator roll, and the applicator roll places and presses the outboard elastic composite onto the substrate web in a desired periodically undulating, curvilinear pattern.

Figure 5:
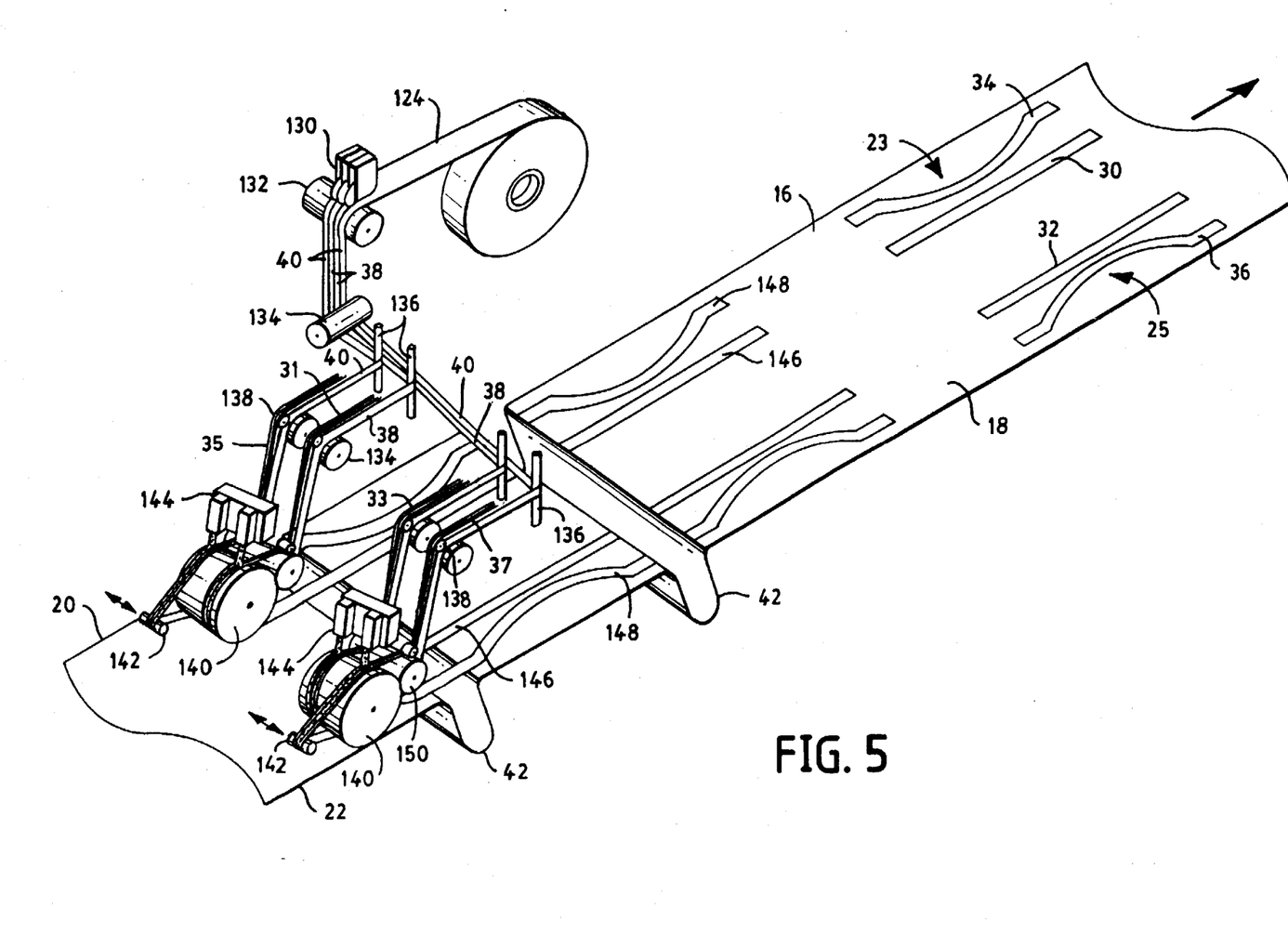
FIG. 5 representatively shows a further technique for providing a plurality of inboard and outboard elastic members employing a single supply roll of carrier web material.

With reference to FIG. 5, a further modification of the technique can include a separating means which is arranged to divide the carrier web 124 into four individual carrier sheets to provide a pair of outboard carrier sheets 40 and a pair of inboard carrier sheets 38. One inboard carrier sheet and one outboard carrier sheet are suitably directed for assembly with the inboard elastic web 33 and the outboard elastic web 37, respectively, and for placement along one side region 18 of the substrate web 14. In addition, the second inboard carrier sheet and the second outboard carrier sheet are suitably directed for assembly with the inboard elastic web 31 and the outboard elastic web 35, respectively, and for placement along the laterally opposite side region 16 of the substrate web.

Having described the invention in rather full detail, it will be readily apparent that various changes and modifications can be made without departing from the spirit of the invention. All of such changes and modifications that are contemplated as being within the scope of the invention as defined by the subjoined claims.

We claim:

1. An apparatus for making an elasticized article, comprising:
   (a) delivering means for supplying a substrate web having a longitudinal direction and a lateral cross-direction;
   (b) first connecting means for applying and attaching an inboard elastic member to said substrate web;
   (c) second connecting means for applying and attaching an outboard elastic member to said substrate web, said outboard elastic member located laterally outboard of said inboard elastic member;
   (d) dividing means configured to separate away a portion of said substrate web and a portion of said outboard elastic member to thereby provide a set of elastics which are arranged in a staggered overlapping relation.

2. An apparatus as recited in claim 1, further comprising means configured for providing said outboard elastic member with a curved configuration on said substrate web.

3. An apparatus as recited in claim 2, wherein said means for providing said outboard elastic member with said curved configuration is constructed to provide said outboard elastic member with a substantially continuously curved configuration on said substrate web.

4. An apparatus as recited in claim 1, wherein said dividing means is constructed to provide said staggered overlapping relation with said outboard elastic member overlapping only a portion of said inboard elastic member.

5. An apparatus as recited in claim 1, wherein said dividing means is constructed to provide said staggered relation with said inboard elastic member overlapping a substantial entirety of said outboard elastic member.

6. An apparatus as recited in claim 1, wherein said dividing means is configured to provide a contoured shape to a terminal side edge of said substrate web, said contoured shape having a depth which is asymmetrical with respect to a longitudinal dimension of said article with a relatively deepest, most inboard portion of said contoured shape located toward an appointed end of said article.

7. An apparatus as recited in claim 6, wherein said dividing means is configured to locate said deepest, most inboard portion of said contoured shape toward an appointed front waistband portion end of said article.

8. An apparatus as recited in claim 7, wherein said dividing means is configured to separate away a substantial portion of a selected longitudinal end region of said outboard elastic member.

9. An apparatus for making an elasticized article, comprising:
   (a) supplying means for providing a substrate web having first and second side regions thereof;
   (b) first connecting means for applying and attaching a first inboard elastic member to said first side region of said substrate web, and a second inboard elastic member to said second side region of said substrate web;
   (c) second connecting means for applying and attaching a first outboard elastic member to said first side region of said substrate web, and a second outboard elastic member to said second side region of said substrate web, each of said outboard elastic members located laterally outboard of said inboard elastic members;
   (d) first dividing means configured to separate away a portion of said first side region of said substrate web and a portion of said first outboard elastic member to thereby provide a first set of elastic members which are arranged in a staggered overlapping relation;
   (e) second dividing means configured to separate away a portion of said second side region of said substrate web and a portion of said second outboard elastic member to thereby provide a second set of elastic members which are arranged in a staggered overlapping relation.

10. An apparatus as recited in claim 9, wherein said first and second connecting means are configured to apply and attach each of said outboard elastic members with a curved configuration on said substrate web.

11. An apparatus as recited in claim 10, wherein said first and second connecting means are configured to apply and attach each of said outboard elastic members with a substantially continuously curved configuration on said substrate web.

12. An apparatus as recited in claim 9, wherein said first dividing means is configured to provide a first reduced outboard elastic member which overlaps only a portion of said first inboard elastic member; and said second dividing means is configured to provide a second reduced outboard elastic member which overlaps only a portion of said second inboard elastic member.

13. An apparatus as recited in claim 9, wherein said first dividing means is configured to provide a first reduced outboard elastic member, a substantial entirety of which is overlapped by said first inboard elastic member; and wherein said second dividing means is configured to provide a second reduced outboard elastic member, a substantial entirety of which is overlapped by said second inboard elastic member.

14. An apparatus as recited in claim 9, wherein
   said first dividing means is configured to provide a first contoured shape to a first terminal side edge of said substrate web, with a depth of said first contoured shape being asymmetrical with respect to a longitudinal dimension of said article and with a deepest, most inboard portion of said contoured shape located toward an appointed end of said article; and
   said second dividing means is configured to provide a second contoured shape to a second terminal side edge of said substrate web, with a depth of said second contoured shape being asymmetrical with respect to said longitudinal dimension of said article and with a deepest, most inboard portion of said second contoured shape located toward said appointed end of said article.

15. An apparatus as recited in claim 14, wherein
   said first dividing means is configured to locate said deepest, most inboard portion of said first contoured shape toward an appointed front waistband portion end of said article; and
   said second dividing means is configured to locate said deepest, most inboard portion of said second contoured shape toward said appointed front waistband portion end of said article.

16. An apparatus as recited in claim 15, wherein
   said first dividing means is configured to separate away a substantial portion of a selected longitudinal end region of said first outboard elastic member; and
   said second dividing means is configured to separate away a substantial portion of a selected longitudinal end region of said second outboard elastic member.

17. An apparatus as recited in claim 16, wherein said second dividing means is configured to provide said second contoured shape in a substantially mirror-image of said first contoured shape.

* * * * *